(12) United States Patent
Uesaka et al.

(10) Patent No.: US 6,846,453 B1
(45) Date of Patent: Jan. 25, 2005

(54) HOUSING OF IMMUNOCHROMATOGRAPHY APPARATUS

(75) Inventors: Yoshihiko Uesaka, Ibaraki (JP); Kumiko Shinohara, Ibaraki (JP); Yuichi Oku, Ibaraki (JP)

(73) Assignee: Nissui Pharmaceutical Co., Ltd. (JP)

( * ) Notice: Subject to any disclaimer, the term of this patent is extended or adjusted under 35 U.S.C. 154(b) by 514 days.

(21) Appl. No.: 09/979,878

(22) PCT Filed: Jun. 8, 2000

(86) PCT No.: PCT/JP00/03728

§ 371 (c)(1),
(2), (4) Date: Nov. 27, 2001

(87) PCT Pub. No.: WO00/77521

PCT Pub. Date: Dec. 21, 2000

(30) Foreign Application Priority Data

Jun. 11, 1999 (JP) .......................................... 11/165051

(51) Int. Cl.⁷ .......................... G01N 21/00; G01N 31/22
(52) U.S. Cl. ......................................................... 422/58
(58) Field of Search .......................................... 422/58

(56) References Cited

U.S. PATENT DOCUMENTS 6,277,650 B1 * 8/2001 Nazareth et al. ............ 436/514

FOREIGN PATENT DOCUMENTS

| EP | 0 291 194 | 4/1988 |
|---|---|---|
| JP | 1-503174 | 10/1989 |
| JP | 6-230009 | 8/1994 |
| JP | 7-55809 | 3/1995 |
| JP | 9-145712 | 6/1997 |
| JP | 2705768 | 10/1997 |
| WO | 95/13541 | 5/1995 |

* cited by examiner

Primary Examiner—Monique T. Cole
(74) Attorney, Agent, or Firm—Lorusso, Loud & Kelly

(57) ABSTRACT

A housing for an immunochromatography apparatus capable of detecting the concentration of an analyte contained in a sample even if it is relatively low in concentration is provided. In the housing 1 of immunochromatography apparatus having an observation window 5, the observation window 5 of the housing 1 is made of a colored transparent plastic material having a transmittance of at least 20%, preferably at least 40%, so that a detection line displayed on a developing strip 2 contained therewithin can be seen therethrough, the other portion of the housing than the observation window 5 is made of a colored transparent plastic material having a transmittance of at least 12%, and the observation window 5 and the housing 1 are simultaneously and integrally molded out of the same plastic material.

3 Claims, 3 Drawing Sheets

HOUSING OF IMMUNOCHROMATOGRAPHY APPARATUS

TECHNICAL FIELD

The present invention relates to a housing for an immunochromatography apparatus useful in simplified clinical diagnosis for detecting a biological substance utilizing the principle of immunochromatography.

BACKGROUND ART

An analytical apparatus utilizing the principle of immunochromatography (hereinafter referred to "as immunochromatography apparatus") is known in the art, as mentioned below. Thus, it comprises:

- a protective case containing a sheet-like developing member or element through which a sample liquid can be developed owing to the capillary phenomenon and/or diffusion;
- an application zone, disposed at one end of the developing member, for applying the sample liquid containing an analyte;
- an water-absorbing zone, disposed at the other end of the developing member, for receiving the liquid that has moved through the developing member owing to the capillary phenomenon;
- a sealed-in zone disposed therebetween at a site closer to the application zone and containing a substance labeled with a substance having a binding affinity for the analyte (an analyte-binding labeled substance):
- a detection zone disposed at a site remoter from the application zone fixed with a substance capable of binding to the analyte, which has a binding affinity for the analyte, but has no same binding affinity as that of the analyte-binding labeled substance, to bind the complex resulting from binding of the analyte to the analyte-binding labeled substance; and
- an observation window formed in the protective case so that the detection zone can be observed.

The "analyte" includes DNAs, RNAs, immunochemically active substances and glycoproteins. The "substance capable of binding to the analyte" includes DNAs, RNAs, immunochemically active substances and lectins. The "label substance" includes metal colloids, dyes, latices, fluorescent substances and enzymes. The "analyte-binding labeled substance" includes DNAs, RNAs, oligonucleotides, biotin, avidins, streptavidin and digoxigenin.

In the analytical procedure using such an immunochromatography apparatus, a sample liquid containing an analyte to be detected or assayed is first applied to the application zone. The sample liquid moves to the sealed-in zone containing an analyte-binding labeled substance owing to the capillary phenomenon. In the sealed-in zone, the analyte-binding labeled substance binds to the analyte through an affinity (for example, immunological affinity) therebetween to give a labeled complex. The labeled complex is developed and migrates through the developing member to the detection zone owing to the capillary phenomenon and/or diffusion and captured by the substance having an affinity therefor as immobilized in the detection zone. The label, or marker, of the labeled complex captured in the detection zone is measured or detected by visual observation or by some other means through the observation window of the protective case, whereby the analyte contained in the sample liquid can be quantitated or judged for the presence or absence thereof.

Another immunochromatography apparatus, such as mentioned below, is also known. Thus, a sheet-like developing member through which a sample liquid can be developed owing to the capillary phenomenon and/or diffusion is contained in a protective case, one end of the developing member is provided with an application zone for applying an analyte-containing sample liquid, and the other end is provided with an absorption zone for receiving the liquid that has migrated through the developing member owing to the capillary phenomenon. Between the zones, there is disposed, at a site closer to the application zone, a sealed-in zone containing a substance labeled with a substance having a binding affinity for the analyte and a substance resulting from coupling of a binding substance differing from the above-mentioned analyte-binding substance but having a binding affinity for the analyte with a binding label substance differing from the above-mentioned label substance. On the side remoter from the application zone, there is disposed a detection zone with a substance immobilized therein and capable of binding to the above binding label substance to thereby bind to a complex composed of the analyte, the analyte-binding substance-labeled substance and the analyte-binding substance coupled with the above binding label substance. The protective case of the immunochromatography apparatus is provided with an observation window so that the detection zone can be observed. For knowing the result of the analysis using this immunochromatography apparatus, too, the label captured in the detection zone is measured or detected through the observation window of the protective case by visual observation or by some other means, whereby the analyte contained in the sample liquid can be quantitated or judged for the presence or absence thereof.

This immunochromatography apparatus is characterized in that the reagents contained in the apparatus are maintained in a dry state during storage before use, hence can be stored at room temperature for a prolonged period of time. Analyses using such immunochromatography apparatus make it possible for a doctor or medical practitioner himself or herself to immediately test a sample collected by him or her, so that the doctor can make a diagnosis comprehensively in a short time based on the clinical symptoms of a patient and the immunological test results. Thus, advantageously, the timing of treatment will scarcely be lost.

As regards the housing for such immunochromatography apparatus, the following technologies are known in the art.

Japanese Patent Application No. 2705768 teaches that a strip or sheet comprising a dry porous immunochromatographic carrier material should be contained in a hollow housing having an opening for detection. The strip or sheet is backed with a transparent sheet made of a plastic material or sandwiched between two plastic material sheets, at least one of which is transparent, and disposed adjacent to the opening so that moisture or the sample liquid can be prevented from entering the housing inside through the opening. According to the above patent, the housing material is opaque or semitransparent and at least one of the plastic sheet materials is transparent.

Japanese Patent Application No. 2825349 teaches that a sample liquid should be taken from one end of an absorbent member for accommodating sample and caused to move to the place of an absorbent member for accommodating sample covered by a housing and the analyte in the sample be observed through a reading window provided on the housing and that the observation window of the housing should be covered with a cap during sample taking and, after sample taking, the cap be removed and placed on the sample taking side.

As for the technology of displaying a detection line in the observation window of an immunochromatography apparatus, the prior art includes the following.

In JP-A No. 230009/1994, an immunoassay tool is shown in which an indicator capable of changing its color upon passage of a liquid sample and retaining the changed color for a long period of time is immobilized in a judging/displaying part to thereby cause the site of immobilization to retain the indicator for a long period of time and by which whether the test liquid has passed the observation window or, in other words, whether the judgment has become possible, can be established.

JP-A No. 145712/1997 discloses an immunochromatography apparatus in which the upper surface of an immunochromatographic material having a water-insoluble colored material immobilized thereon is covered with a water-soluble, optically opaque substance so that whether a solution applied to the chromatography apparatus has passed the measurement area can be displayed to thereby indicate that the apparatus is now in a condition ready for judgment and in which the condition ready for judgment is thus indicated by dissolution of the covering substance.

It is a problem with the prior art immunochromatography apparatus that when the concentration of a substance to be detected is low, the substance cannot be detected or different testers may give different judgment results although when the concentration of the test substance in the sample solution is not lower than a certain level, the substance can be detected through the observation window.

In the prior art immunochromatography apparatus, the housing containing a developing strip is opaque or semitransparent, so that when a sample solution is developed through a developing strip, how far the development has advanced can be confirmed only through the observation window or a confirmation window for confirming the extent of development of the sample solution. If the sample solution is a viscous liquid, the liquid may stop penetrating in the middle of the strip or may be too late getting to the detection site. If the liquid fails to arrive at the detection site within a predetermined period of time, the test, which is in reality positive, may possibly be judged negative.

In the prior art chromatography apparatus, the developing strip is exposed in the window or, even when the developing strip is covered with a transparent sheet, the window is not in a completely closed condition, so that the sample solution or the like may be splashed on the window by mistake or without being noticed or the sample solution or the like may further enter the inside, contaminating the developing strip or causing an erroneous diagnosis.

DISCLOSURE OF INVENTION

Accordingly, it is an object of the present invention to provide a housing for an immunochromatography apparatus which makes it possible to accurately detect a test substance contained in a sample even when the concentration thereof is low, prevents the sample solution or the like, even when splashed onto the observation window by mistake or without being noticed, from penetrating into the strip inside the housing, gives stable judgment results even when it is used by an unskilled person, and enables estimation of the condition ready for judgment from the whole apparatus.

The housing for an immunochromatography apparatus according to the present invention, by which the above object can be accomplished and which has an observation window, is characterized in that the observation window of the housing is a sealed one made of a colored transparent plastic material having a thickness such that the transmittance is not less than 20%, preferably not less than 40%, so that a detection line displayed on a developing strip contained within the housing can be seen through the window, that, on the observation window side, the housing is made of a colored transparent plastic material having a thickness such that the transmittance is not less than 12% and that, on the observation window side, the housing and the observation window are simultaneously and integrally molded out of the same plastic material.

The color of the observation window is preferably selected so that it may show an optical effect improving the visibility of the detection line color on the developing strip, which is to be seen through the observation window.

The housing for immunochromatography apparatus according to the invention is colored but transparent and the observation window thereof is covered with the plastic material integrally molded with the housing, so that the detection line, which indicates that an immunological substance is contained on the developing strip, can be readily confirmed upon observation through the observation window made of the colored transparent plastic material.

The capability of being easily observed (visibility) of the detection line color resulting from binding of a label substance can effectively improved by utilizing the color contrast effect. In particular, when a complementary color hue is matched, the chroma of each color is increased and the overlapping portion is particularly emphasized. Therefore, it is preferred that the color hue of the housing be selected so that it is complementary to the color hue of the marker label substance contained on the developing strip. By doing so, it becomes possible to detect an immunological substance even when the concentration thereof is so low that it cannot be detected through a colorless transparent window.

The housing for immunochromatography apparatus according to the invention is colored and transparent, so that the state or extent of development of the sample solution can be confirmed by seeing through the housing.

In the housing for immunochromatography apparatus according to the invention, the observation window is covered with the plastic material which molds simultaneously and integrally the observation window and the housing. Therefore, even when the sample solution is splashed onto the window by mistake or without being noticed, the solution cannot enter the strip occurring in the housing. For the above reason, the risk of touching an infectious sample by mistake, such as incurred with the prior art housings, is low.

BEST MODES FOR CARRYING OUT THE INVENTION

Figure 1:
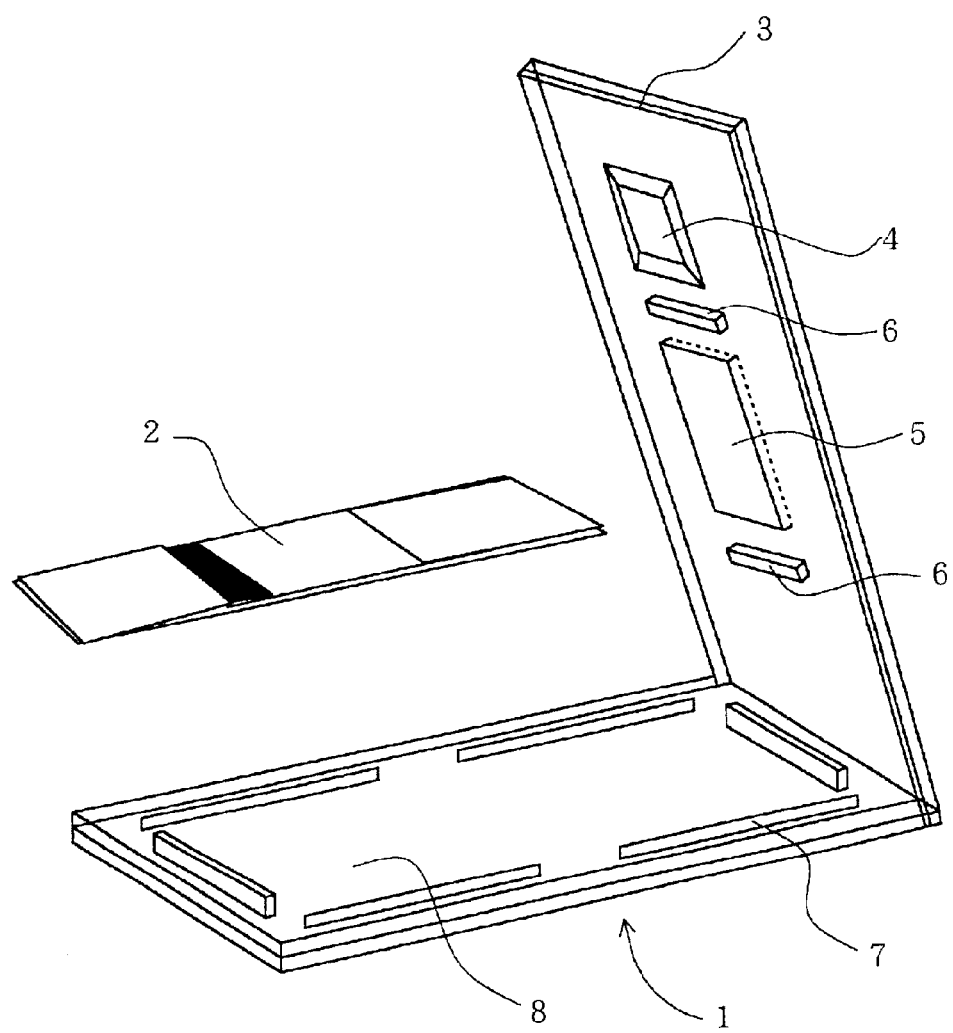
FIG. 1 is a perspective view of a housing of an immunochromatography apparatus according to the present invention and a developing strip to be contained therein.
Figure 2:
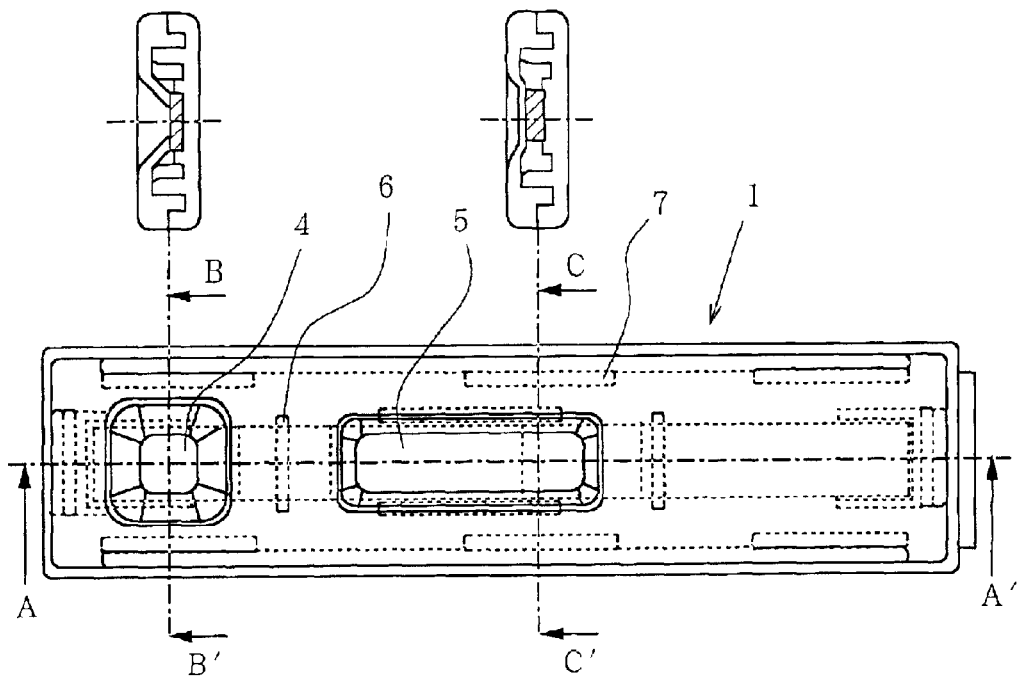
FIG. 2 is a plan view thereof and includes a sectional view along B'–B and a sectional view along C'–C.
Figure 3:
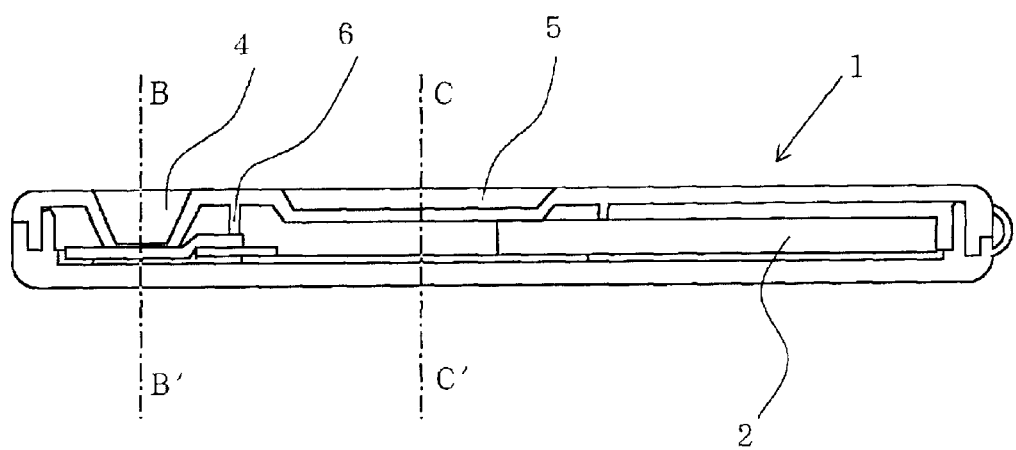
FIG. 3 is a sectional view along the line A–A' of FIG. 2.

In FIG. 1 to 3, 1 stands for a housing. It comprises an upper cover 3 and a lower container 8, which are molded integrally via a hinge structure. The upper cover 3 is provided with an observation window 5 for observing a detection line displayed on a developing strip 2. The observation window 5 is colored and transparent and is covered with the plastic material which molds simultaneously and integrally the observation window 5 and the housing 1. On the inside of the upper cover 3, there are provided several protrusions 6 for supporting the developing strip 2 from the upper side. In the vicinity of one terminal of the upper cover 3, there is provided a sample addition window 4 for supplying a sample solution. Protrusions 7 are strip guards for fixing the four sides of the developing strip 2 and are integrally molded with the lower container 8 so that they stand up from the lower container surface.

EXAMPLE 1

When colloidal gold is used as a marker label to be contained in a developing strip, colloidal gold shows a red—red purple hue (Munsell color atlas: 2.5 PR-2.5 R) and a maximum absorption wavelength of 510–540 nm.

A high level of visibility can be obtained by selecting, for the developing strip, a blue green—green (Munsell color atlas: 2.5 BG-2.5 G) housing and an observation window of the housing which, from the shade of color viewpoint, shows a high spectral reflectivity at 500–560 nm, preferably at about 510–540 nm, as measured by using a Minolta Co. Ltd. spectral calorimeter.

While the label or marker substances to be used in immunochromatography include colored liposomes, colored polymer beads, metal-containing dye particles, enzymes and so forth, it is possible, by using the same principle as in this Example 1, to select the color hue of the housing so that it may be suited for the label substance used or the product resulting from enzymatic conversion of a substrate.

EXAMPLE 2

Colored housings were evaluated using an immunochromatographic strip for detecting the type B hepatitis surface antigen (HBsAg) with colloidal gold particles as the label substance. Five housings differing in color, inclusive of the blue green—green colored housing described in Example 1, were prepared (No. 1 to No. 5: light purple, jade green, white, light green, transparent) and the immunochromatographic strip for detecting HBs antigen was set in each housing. The color, the hue (Munsell system), the transmittance of the housing body and the transmittance of the observation window for each of the five housings were as shown below in Table 1. The transmittance measurement was performed at the wavelength of 660 nm using a Shimadzu Co. Ltd. model UV-1200 spectrophotometer. The transmittance of the body proper and of the observation window of each housing was determined using a quartz cell as a blank (transmittance 100%). The transmittance $\angle$ is expressed as follows:

$$\angle = \Phi_t \Phi_i$$

where $\Phi_i$ is the luminous flux incident on the specimen and $\Phi_t$ is the transmitted luminous flux.

HBsAg at a concentration of 3.75 ng/ml (note: the commercial kits are said to have a detection sensitivity of 5–10 ng/ml, hence 3.75 ng/ml is a very low concentration) was allowed to react on each developing strip and the depth of the color of the detection line appearing on the developing strip was evaluated by 20 testers or panelists by visual observation, and the colored housings were ranked accordingly. The sensory test results given for the HBsAg concentration of 3.75 ng/ml by each of the 20 panelists are graphically shown in FIG. 4, with the order of visibility being taken on the ordinate and the individual panelists on the abscissa. As the results shown indicate, 85% of the panelists (17/20) judged that the housings No. 2 or No. 4 showed the highest visibility when the detection line appeared very pale (when the HBsAg concentration was 3.75 ng/ml).

TABLE 1

| Housing Species | Body portion | Observation window | Color (conventional) | Munsell system |
|---|---|---|---|---|
| No. 1 | 3.3% | 65.4% | Light purple | 7.9 P 6.4/0.7 |
| No. 2 | 17.9% | 71% | Jade green | 1.9 BG 7.2/3.2 |
| No. 3 | 6.3% | 65.3% | White | 2.2% 7.7/0.1 |
| No. 4 | 32.5% | 84% | Light green | 1.6 G 6.8/4.7 |
| No. 5 | 24.3% | 65.7% | Transparent | 2.9 Y 7.9/0.1 |

Munsell system: hue ring, lightness/chroma
G: Green, BG: Blue green, Y; Yellow, P: Purple

EXAMPLE 3

Immunochromatographic strips were prepared by allowing known concentrations of HBsAg (5 ng/ml, 2.5 ng/ml) to react on developing strips to cause a detection line to appear on each strip. Very thin plastic filters (thickness 0.25 mm, transmittance 80%) were piled up on each immunochromatographic strip to give a simulated housing membrane corresponding to a housing with a transmittance as shown below in Table 2. The number of filters laid up was increased one by one from 1 to 16. The thus-obtained 16 simulated housing membranes showing different transmittance values were examined for two items, namely the visibility of the sample developed and the test lines (antibody concentrations of 5 ng/ml and 2.5 ng/ml). The transmittance measurement was carried out at the wavelength of 660 nm using a Shimadzu model UV-1200 spectrophotometer. The results obtained are shown below in Table 2.

TABLE 2

| | | | Test line visibility | |
|---|---|---|---|---|
| Number of filters | Transmittance | Visibility of sample development | Positive limit 5 ng/ml | Visible limit concentration 2.5 ng/ml |
| 1 | 79.7% | good | Good | ○ |
| 2 | 55.8% | Good | Good | Δ |
| 3 | 38.5% | ○ | Δ | |
| 4 | 26.8% | | Δ | X |
| 5 | 19.6% | Development generally distinguishable | | |
| 6 | 14.5% | Development generally distinguishable | X | |
| 7 | 11% | X (Development distinction) | | |
| 8 | 8.6% | | | |
| 9 | 6.7% | Δ (Content distinction) | | |
| 10 | 5.4% | | | |
| 11 | 4.3% | X (Content distinction) | | |
| 12 | 3.3% | | | |
| 14 | 2.4% | | | |
| 16 | 1.6% | | | |

○: Visible, Δ: Distinction difficult, X: Distinction impossible

From the visibility confirmation results on the occasion of sample development as shown in Table 2, it is seen that the transmittance of the housing proper at which the condition of development can be confirmed is not less than 12% of test line visibility confirmation results shown in Table 2, it is also seen that the transmittance of the observation window should be not less than 20%, preferably not less than 40%.

INDUSTRIAL APPLICABILITY

The housing for immunochromatography apparatus according to the invention is colored and transparent and the observation window thereof is covered with the plastic material from which the observation window and housing are molded integrally. As a result, the detection line indicative of the fact that an immunological substance is contained on the developing strip can readily be confirmed when seen through the transmitting window made of the colored, transparent plastic material.

The easiness in seeing (or the visibility of) of the detection line color resulting from binding of a label or marker substance can be effectively improved by contrasting the color with the color of the observation window. In particular, when color hues in a complementary color relation are matched simultaneously, the chroma of each color is potentiated and the overlapping portion is emphasized. Utilizing this principle, a housing having a color hue complementary to the color hue of the marker label substance contained on the developing strip can be selected for use. Such selection makes it possible to detect an immunological substance contained in the sample liquid even when the concentration thereof is Low.

Since the housing for immunochromatography apparatus according to the invention is colored and transparent, the state of development of the sample solution can be confirmed through the housing at any site on the developing strip.

Since the observation window of the housing for immunochromatography apparatus according to the invention is covered with the plastic material used for integral molding of the observation window and housing, the sample solution, if splashed onto the window by mistake or without being noticed, cannot enter the strip within the housing, so that erroneous diagnoses can be prevented.

What is claimed is:

1. A housing for an immunochromatography apparatus, having an observation window, wherein the observation window of said housing is a sealed window made of a colored transparent plastic material having a thickness such that the transmittance amounts to at least 20% so that a detection line displayed on a developing strip contained therewithin can be seen therethrough, wherein the color of the observation window is selected so that it has an optical effect improving the visibility of the color of that detection line displayed on the developing strip which is to be seen through the observation window, wherein on the observation window side, the housing is made of a colored transparent plastic material having a thickness such that the transmittance amounts to at least 12%, and wherein on the observation window side, the housing is molded simultaneously and integrally with the observation window out of the same plastic material.

2. A housing for an immunochromatography apparatus as claimed in claim 1, wherein the transmittance of the observation window is not less than 40%.

3. A housing for an immunochromatography apparatus as claimed in claim 1, wherein the color having an optical effect improving the visibility of the color of that detection line on the developing strip which is to be seen through the observation window is in a complementary color relation with the color of the detection line.

* * * * *

UNITED STATES PATENT AND TRADEMARK OFFICE
CERTIFICATE OF CORRECTION

PATENT NO. : 6,846,453 B1
DATED : January 25, 2005
INVENTOR(S) : Uesaka et al.

Figure 4:
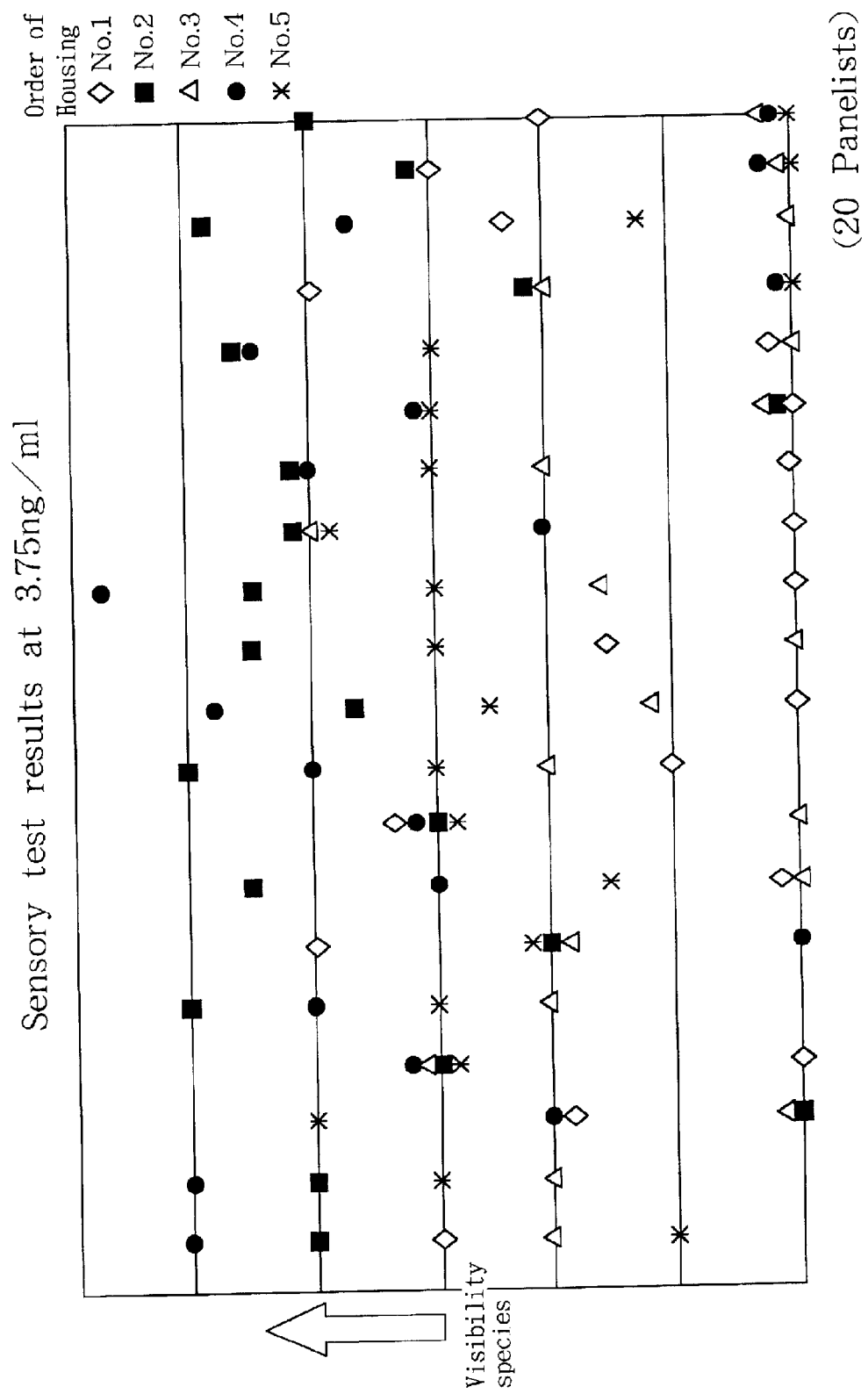

It is certified that error appears in the above-identified patent and that said Letters Patent is hereby corrected as shown below:

Column 4,
Between lines 57 and 58, please insert the following:
-- Fig. 4 is a graph showing sensory test results given for the HBsAG concentration of 3.75 ng/ml by each of 20 panelists. --

Signed and Sealed this

Twelfth Day of July, 2005

JON W. DUDAS
*Director of the United States Patent and Trademark Office*

UNITED STATES PATENT AND TRADEMARK OFFICE
CERTIFICATE OF CORRECTION

PATENT NO.   : 6,846,453 B1
DATED        : January 25, 2005
INVENTOR(S)  : Uesaka et al.

It is certified that error appears in the above-identified patent and that said Letters Patent is hereby corrected as shown below:

Column 5,
Line 50, "$\Phi_t$" should read -- $\Phi_i$ --.

Signed and Sealed this

Twenty-third Day of August, 2005

JON W. DUDAS
*Director of the United States Patent and Trademark Office*